US008419733B2

(12) United States Patent
Hajianpour

(10) Patent No.: US 8,419,733 B2
(45) Date of Patent: Apr. 16, 2013

(54) EXTERNAL FIXATION APPARATUS WITH ADJUSTABLE PIN CLAMPING MEANS

(75) Inventor: Mohammed Ali Hajianpour, Fort Lauderdale, FL (US)

(73) Assignee: Nutek Orthopedics, Inc., Fort Lauderdale, FL (US)

( * ) Notice: Subject to any disclaimer, the term of this patent is extended or adjusted under 35 U.S.C. 154(b) by 285 days.

(21) Appl. No.: 12/800,511

(22) Filed: May 17, 2010

(65) Prior Publication Data
US 2010/0318084 A1 Dec. 16, 2010

Related U.S. Application Data

(63) Continuation-in-part of application No. 11/893,582, filed on Aug. 16, 2007, now Pat. No. 7,717,916.

(51) Int. Cl.
*A61B 17/60* (2006.01)
(52) U.S. Cl.
USPC .............................. 606/59; 606/54
(58) Field of Classification Search .............. 606/53–59, 606/71, 74
See application file for complete search history.

(56) References Cited

U.S. PATENT DOCUMENTS

| | | | | |
|---|---|---|---|---|
| 4,127,119 A | * | 11/1978 | Kronner | 606/56 |
| 4,475,550 A | * | 10/1984 | Bremer et al. | 606/165 |
| 4,643,177 A | * | 2/1987 | Sheppard et al. | 602/40 |
| 4,920,959 A | * | 5/1990 | Witzel et al. | 606/53 |
| 5,062,844 A | * | 11/1991 | Jamison et al. | 606/54 |
| 5,393,161 A | * | 2/1995 | Mata et al. | 403/133 |
| 5,591,169 A | * | 1/1997 | Benoist | 606/59 |
| 5,607,426 A | * | 3/1997 | Ralph et al. | 606/287 |
| 5,779,703 A | * | 7/1998 | Benoist | 606/54 |
| 5,885,282 A | * | 3/1999 | Szabo | 606/56 |
| 6,235,803 B1 | * | 5/2001 | Weiser et al. | 521/60 |
| 6,860,883 B2 | * | 3/2005 | Janowski et al. | 606/56 |
| 7,361,176 B2 | * | 4/2008 | Cooper et al. | 606/54 |
| 2003/0225407 A1 | * | 12/2003 | Estrada, Jr. | 606/54 |
| 2010/0305568 A1 | * | 12/2010 | Ross et al. | 606/56 |
| 2011/0288549 A1 | * | 11/2011 | Steiner et al. | 606/56 |

* cited by examiner

*Primary Examiner* — Eduardo C Robert
*Assistant Examiner* — Lynnsy Schneider
(74) *Attorney, Agent, or Firm* — Ronald V. Davidge

(57) ABSTRACT

An external fixation device for holding bone fragments in place includes a housing having a number of rotationally adjustable pin holders, each of which is held by a clamping member that simultaneously clamps the pin holder within an internal mounting surface of the housing and a bone pin within the pin holder. A first embodiment includes a number of pin mounting structures, each of which can include a single pin holder. A second embodiment includes one or two pin mounting structures, each of which holds a row of pin holders that is clamped in place by a single clamping member. Other embodiments are formed by fastening together a group of elements to form different housing configurations.

11 Claims, 7 Drawing Sheets

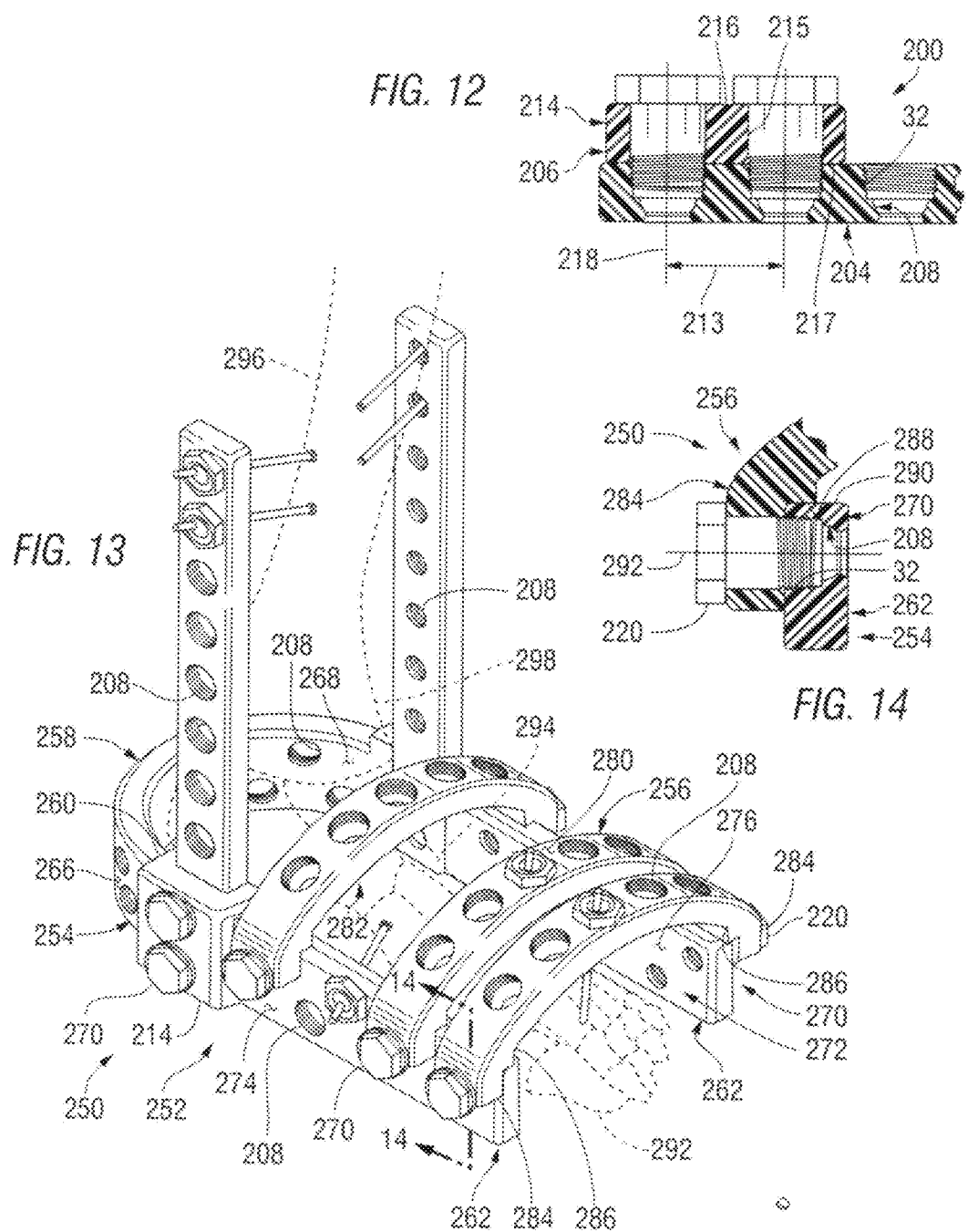

EXTERNAL FIXATION APPARATUS WITH ADJUSTABLE PIN CLAMPING MEANS

CROSS-REFERENCE TO A RELATED APPLICATION

This is a continuation in part of a U.S. patent application Ser. No. 11/893,582, filed Aug. 16, 2007, now issued as U.S. Pat. No. 7,717,916 B2.

BACKGROUND OF THE INVENTION

1. Field of the Invention

This invention relates to apparatus for the external fixation of fractured bones, and, more particularly, to such apparatus having means for adjustably mounting and clamping a number of bone pins to a housing.

2. Summary of the Background Art

External fixation often provides the best method for holding bone fragments in place during the healing of a severe bone fracture, in which multiple bone fragments are formed. In the external fixation process, bone pins or wires ate surgically attached to the individual bone fragments and to intact sections of bone, so that a desired alignment of multiple fragments can be maintained during the healing process. The individual bone pins or wires are also attached to a frame that is external to the body to be held in a fixed configuration. Then, after the bone fragments have joined to one another in a satisfactory manner, the bone pins or wires are removed from the bones and from the body in another surgical procedure. With external fixation, an ability to hold individual bone fragments in place often makes in possible to achieve results that cannot be achieved using other conventional techniques, such as casting.

Since serious bone fractures can occur in many different ways in various parts of the body, forming various configuration of bone fragments, it is highly desirable that a device for external fixation should be configured in a variety of different ways, reducing the number of different types of fixation devices that need to be held in inventory to meet expected demands. To this end, the patent literature includes a number of descriptions of fixation devices that can be assembled from multiple elements in various ways or that can be adjusted to provide various configurational features.

One method to obtain this kind of flexibility has been to provide a plate having a number of holes defining locations in which bone pins or wires may be clamped, with only a variable subset of the holes being used in the treatment of a typical fracture. For example, U.S. Pat. No. 7,153,303 describes a fixture including several holes for clamping members to hold bone pins disposed within an elongated portion and a number of holes in a rectangular pattern, which can accommodate a variety of pin configurations. Such an arrangement is used, for example, to fasten the elongated portion of the fixture to the shaft of the radius bone within the arm and to attach vatious fragments within a broken wrist to a pattern of pins clamped within the rectangular array. A configuration for applying external fixation to a fractured tibia is also described as including a frame an elongated lower section for fastening the frame to the shaft of the tibia using bone pins extending along a straight line and an arcuate section extending from each side of the upper end of the elongated lower section for clamping bone pins extending into bone fragments within the upper portion of the tibia. U.S. Pat. No. 5,779,703 describes a bone organizer having a number of holes through which wires are attached to bone fragments.

Another method for obtaining flexibility within an external fixation device is to provide a number of clamping elements holding one or more bone pins, with the clamping elements being attached to one another by devices providing for pivotal adjustment. For example, U.S. Pat. No. 5,624,440 describes a fixture including a number of clamping elements, each of which clamps a pair of bone pins extending parallel to one another and a rod to which the clamping elements are attached by means of a pair of pivoting clamps providing for rotational adjustment and clamping about two axes perpendicular to one another. U.S. Pat. No. RE34,985 describes a fixation device having a pair of elongated carriers, each of which supports a pair of bone screws that are movable along the carrier by rotating a spindle. The carriers are joined to one another by a connector including a rigid rod and a ball at each end. The balls are received by partly spherical sockets that can be fixed relative to the balls through screws. U.S. Pat. No. 4,554,915 describes an external fixation frame including a fixation block from which one or more arms extend, with a ball and socket joint connecting each arm to the block for universal movement thereabout. Setscrews are provided for tightening the ball and socket joints. International Pat. Appl. Pub. No. WO 91/111 describes a fixation device having a pair of clamping members, each of which includes a row of holes into which bone pins may be inserted and clamped, with the clamping members being connected by a tube, into which a rod extends from one of the clamping members, while a ball from the other connecting member extends into a partially spherical hole within the tube. Setscrews are provided for clamping the rod and ball in place within the tube.

What is needed is a bone fixation device having the flexibility of adjusting the angle at which individual bone pins extend from a housing or frame, preferably with such an adjustment being provided through a clamping device that simultaneously clamps both the linear extension of the bone pin, along its length, and its angle relative to the housing or frame.

SUMMARY OF THE INVENTION

In accordance with one aspect of the invention, apparatus is provided for external fixation of bone fragments, with the apparatus including an inner frame member and an outer frame member. The inner frame member includes a straight section having an inner surface, an outer surface, and a plurality of pin mounting structures, Each of the pin mounting structures includes a internal mounting surface, an aperture extending from the internal mounting surface to the inner surface, and a threaded surface extending from the internal mounting surface to the outer surface. The internal mounting surface, the aperture, and the threaded surface are aligned coaxially an axis of the internal mounting surface. The axes of adjacent pin mounting structures within the inner frame member are each separated along a length of the straight section by a first separation distance. The first outer frame member includes a first attachment section having an inner surface, an outer surface, and two attachment holes. Each attachment hole extends along an axis from the inner surface to the outer surface, wherein the axes of are separated along a width of the attachment section by the first separation distance. The outer frame member is attached to the first inner frame member with the two attachment holes aligned with two adjacent pin mounting structures along the inner frame member.

Since the axes of all of these adjacent pin mounting structures are separated by the first separation distance, the outer frame may be attached to the inner frame at any two of the adjacent pin mounting structures, while other pin mounting structures are used for the attachment of bone pins extending through pin holder clamped in place within the internal mounting surfaces therein by clamping members engaging the threaded surfaces therein. Each of the pin holders includes a slot extending perpendicular to a pin hole, in which a bone pin extends, and across the pin hole, forming a deformable portion of the pin holder.

In accordance with another aspect of the invention, a kit for building apparatus for the external fixation of bone fragments is provided. The kit includes the outer frame member, a plurality of the inner frame members, a plurality of the attachment bolts, a plurality of the bone pins, a plurality of the pin holders, and a plurality of the clamping members.

In accordance with yet another aspect of the invention, a method for building apparatus for the external fixation of bone fragments is provided. The method includes attaching a plurality of the inner frame members to an outer frame member with a plurality of the attachment bolts.

One embodiment of the invention is particularly suited for the external fixation of a long bone having a number of bone fragments formed in the fracture area, such as at one of the ends of the long bone. In this embodiment, the outer frame member includes a pair of arcuate sections, extending in opposite directions from an intermediate attachment section to an end attachment section, providing for the attachment thereto of up to three inner frame members. For example, the fixation apparatus is placed with the outer frame member extending around the fracture area and with the inner frame members extending along the shaft of the bone. Bone pins surgically fastened into the bone fragments are held in pin mounting structures within the arcuate sections of the outer frame members, while bone pins surgically fastened into the shank portion of the bone are held in the pin mounting structures within the straight sections of the inner frame members. One or more additional outer frame members may be added to improve the strength and rigidity of the apparatus, with the outer frames extending in a common direction or in opposite directions.

Another embodiment of the invention is particularly suited for the external fixation of fractured bones within a foot. In this embodiment, the outer frame member includes a single arcuate section, with an attachment section disposed at each end of the arcuate section, and with a straight section extending forward from each of the attachment sections. An inner frame member extends upward from each of the attachment sections, and a plurality of cross members are fastened to extend between the straight sections of the outer frame member. For example, bone pins surgically attached to the leg bones are held in the pin mounting structures within the inner frame members, while bone pins surgically attached to bones within the foot are held in pin mounting structures within the straight sections of the outer frame member and within curved sections of the cross members.

BRIEF DESCRIPTION OF THE FIGURES

FIG. 12 is a fragmentary cross-sectional elevation of the bone fixation apparatus of FIG. 11, taken as indicated by section line 12-12 therein;

FIG. 13 is a perspective view of bone fixation apparatus built in accordance with a fourth embodiment of the invention from a number of interchangeable parts;

FIG. 14 is a fragmentary cross-sectional elevation of the bone fixation apparatus of FIG. 13, taken as indicated by section lines 14-14 therein;

DETAILED DESCRIPTION OF THE INVENTION

Figure 1:
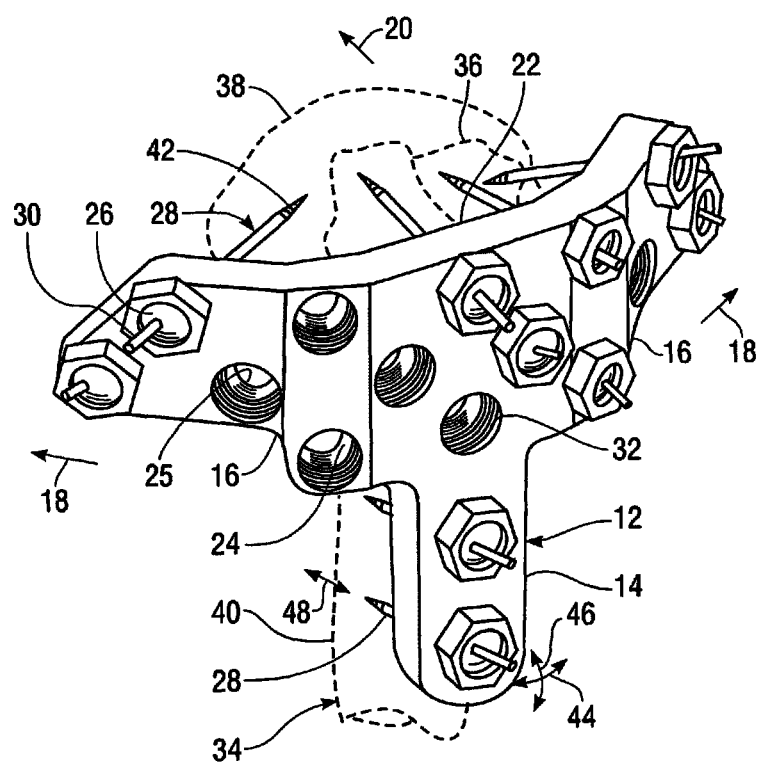
FIG. 1 is a perspective view of a device for external fixation of bone fragments, built in accordance with a first embodiment of the invention.

FIG. 1 is a perspective view of a device 10 for the external fixation of bone fragments, built in accordance with a first embodiment of the invention. The device 10 includes a housing 12 having a vertically elongated central portion 14 and a lateral portion 16 extending outward, in the directions of arrows 18, and rearward, in the direction of arrow 20, from each side of an upper end 22 of vertically elongated central portion 14: The vertically elongated central portion 14 includes a first plurality of the internal mounting surfaces 24; each of which extends outwardly from an aperture 25 within the housing 12, while each lateral portion 16 includes at least one of the internal mounting surfaces 24 extending from an aperture 25. Some of the internal mounting surfaces 24 mount pin holders 26 holding bone pins 28, with the pin holders 26 being held in place by clamping members 30 engaging threaded surfaces 32 of the housing 12. This arrangement provides for the placement of bone pins 28 at various levels extending downward from the upper end 22 of the vertically elongated central portion 14, with the lateral portions 16 being inclined relative to one another so that bone pins 28 can extend inward around a fracture area from these portions 16.

In the example of FIG. 1, the device 10 is shown with various bone pins 28 attached to a fractured humerus bone 34, holding a number of fragments 36 in place at an upper end 38 of the humerus bone 34, with bone pins 28 held within the vertically elongated central portion 14 of the housing 12 attached to the shaft portion 40 of the humerus bone 34. Each of the bone pins 28 includes a threaded end 42 that is driven into engagement with a portion of the bone 34 by a driving tool (not shown) rotating a non-circular surface (not shown) at an end of the bone pin 28 opposite the threaded end 42. After the bone pin 28 is fastened into place, the bone pin 28 is preferably cut off outwardly adjacent the pin holder 26 in which it is held to limit the distance through which the bone pin 28 extends outwardly from the device 10. The configuration of the device 10 is adjustable in several ways, with pin holders 26 being placed in a subset of the internal mounting surfaces 24, so that bone pins 28 are placed at locations appropriate for the external fixation of a particular fractured bone. In addition, the individual pin holders 26 are angularly adjustable so that each bone pin 28 can be adjusted and clamped in place through a vertical angle of adjustment 44 and through a horizontal angle of adjustment 46, with the bone pin 28 additionally being adjustable along its axis in the directions of arrows 48.

Figure 2:
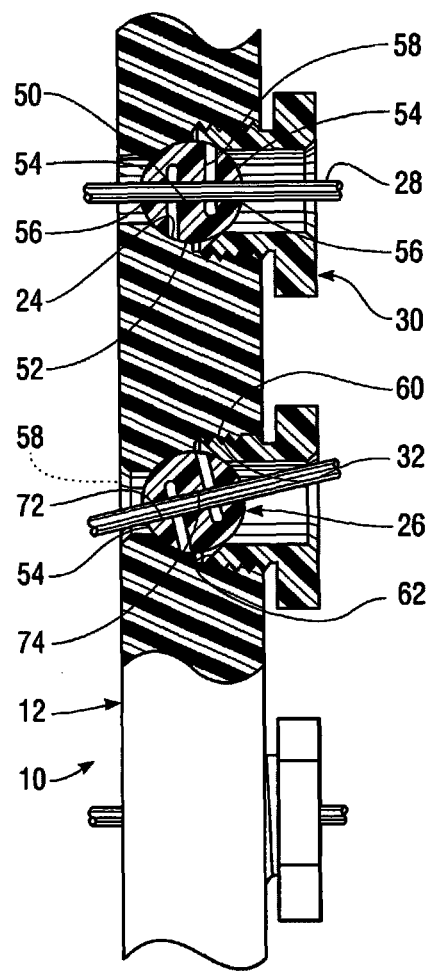
FIG. 2 is a fragmentary and partly cross-sectional lateral elevation of the device of FIG. 1.

FIG. 2 is a fragmentary and partly cross-sectional lateral elevation of the device 10, particularly showing features of the internal mounting surfaces 24 within the housing 12, of the pin holders 26, and of the clamping members 30. Each of the pin holders 26 includes a pin mounting hole 50, a spherically rounded surface 52 engaging an internal mounting surface 24 within the housing, and deformable portions 54 at each end 56 of the pin mounting hole 50. Each of the deformable portions 54 is formed by a slot 58 extending inward in a direction perpendicular to the pin mounting hole 50, extending across the pin mounting hole 50 and part of the way across the pin holder 26. Each of the of clamping members 30 clamps a pin holder 26 in place within the housing 12 and deflects the deformable portions 54 of the pin holder 26 to hold the pin 28 in place within the pin holder 26. Each clamping member 30 includes a threaded surface 60 and an annular surface 62 engaging a deformable portion 54 of a pin holder 26. The threaded surface 60 of each of the clamping members 30 engages one of the threaded surfaces 32 of the housing 12.

Thus, each of the bone pins 28 extends through an aperture 25 within the housing 12 at angles, in horizontal and vertical planes relative to the housing 12, that can be varied by rotation of the spherically rounded surface 52 of the pin holder 26 through which the bone pin 28 extends within the internal mounting surface 24. A bone pin may extend in a direction perpendicular to the aperture 25 or at an angle of inclination relative to such a direction of, for example, up to thirty degrees.

Figure 3:
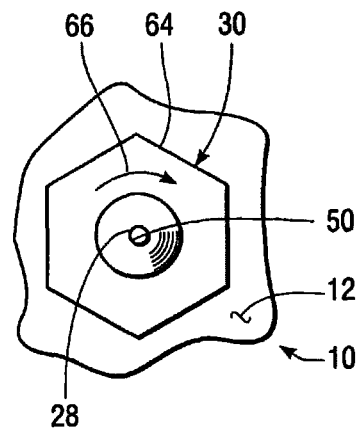
FIG. 3 is a fragmentary front elevation of the device of FIG. 1.

FIG. 3 is a fragmentary front elevation of the device 10, showing one of the clamping members 30, which is provided with a noncircular surface 64 to facilitate rotation of the clamping member 30. As the clamping member 30 is tightened by rotation in a first direction, indicated by arrow 66, an engagement force between the spherically rounded surface 52 of the pin holder 26 clamped in place within the housing 12 by the clamping member 30 and the internal mounting surface 24 within the housing 12 is increased to hold the pin holder 26 in place within the housing 12 and deflection of the deformable portions 54 of the pin holder is increased to hold the bone pin 28 in place within the pin holder 26. As each of the clamping members 30 is rotated opposite the first direction of arrow 66, the engagement force between the spherically rounded surface 52 of the pin holder 26 and the internal mounting surface 24 within the housing 12 is decreased to allow rotation of the spherically rounded surface 52 of the pin holder 26 within the internal mounting surface 24 of the housing 12 and to allow movement of the bone pin 28 within the pin mounting hole 50 of the pin holder 26. For example, the device 10 may be provided with a box wrench (not shown) for loosening and tightening the clamping members 30.

Figure 4:
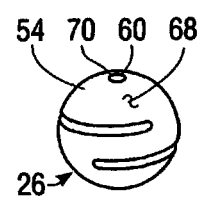
FIG. 4 is a perspective view of a pin holder within the device of FIG. 1.

FIG. 4 is a perspective view of one of one of the pin holders 26, which has a spherical external surface 68. The clamping member 30 includes a pair of slots 58 extending perpendicular to the pin mounting hole 50, inward across the pin mounting hole 50 and partly across the pin holder 26, so that a deformable portion 54 is formed between each end 56 of the pin mounting hole 50 and the slot 58 that is nearer to the end 56.

As shown in FIG. 3, the pin mounting hole 50 extends through a center of the spherical external surface 68, being divided by the slots 58 into a deflectable part 72 within each of the deformable portions 54 and a central part 74 extending between the slots 58. When the clamping member 30 is tightened by rotation in the direction of arrow 66 to increase an engagement force holding the pin holder 26 in place, the deformable portions 54 are deflected inward, bring the deflectable parts 72 of the pin mounting hole 50 out of alignment with the central part 74 thereof, so that the bone pin 28 is clamped in place within the pin mounting hole. Then, when the clamping member is loosened by rotation opposite the opposite the direction of arrow 66 to decrease the engagement force holding the pin holder 20 in place, the deformable portions 54 return outward, so that the deflectable parts 72 of the pin mounting hole 50 return into alighment with the central part 74 thereof, allowing movement of the bone pin 28 within the pin mounting hole 50. For example, the bone pin 28 may be rotated as much as thirty degrees from a central position in which the bone pin 28 extends perpendicularly from the housing 12.

Figure 5:
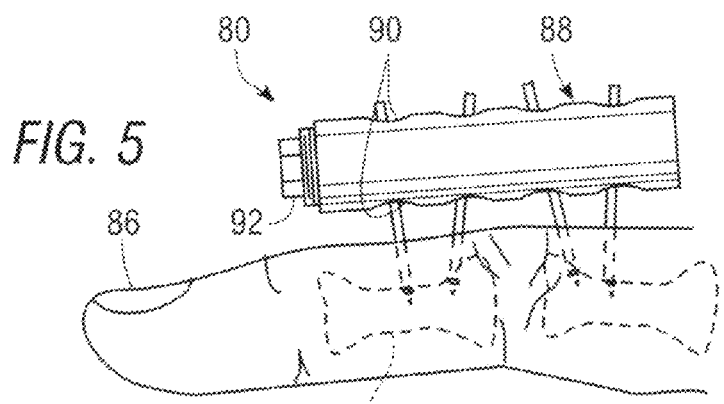
FIG. 5 is a side elevation of a device built in accordance with a first version of a second embodiment of the invention and shown attached to bone fragments within a finger.

FIG. 5 is a side elevation of a device 80 for external fixation of bone fragments, built in accordance with a second embodiment of the invention and shown with pins 82 attached to several fragments of bones 84 within a finger 86. The device 80 includes a housing 88, having a plurality of apertures 90 through which the pins 82 extend, and a first clamping member 92, which is turned to clamp the pins 82 in place within the housing 88.

Figure 6:
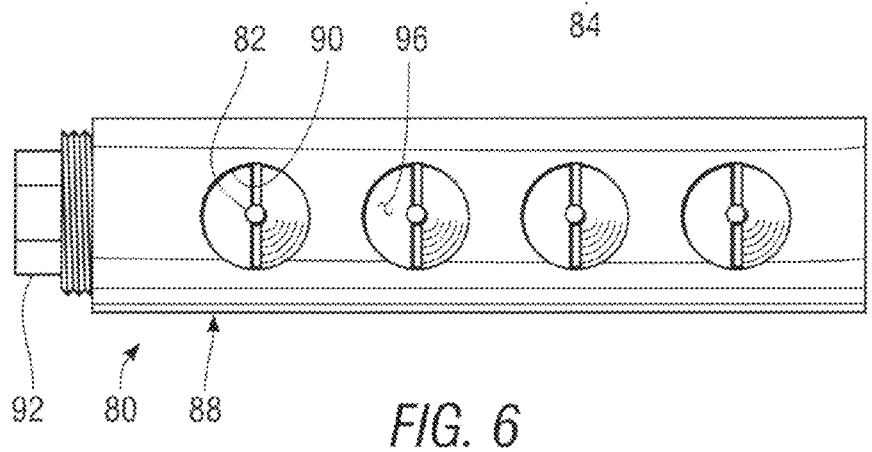
FIG. 6 is a plan view of the device of FIG. 5.
Figure 7:
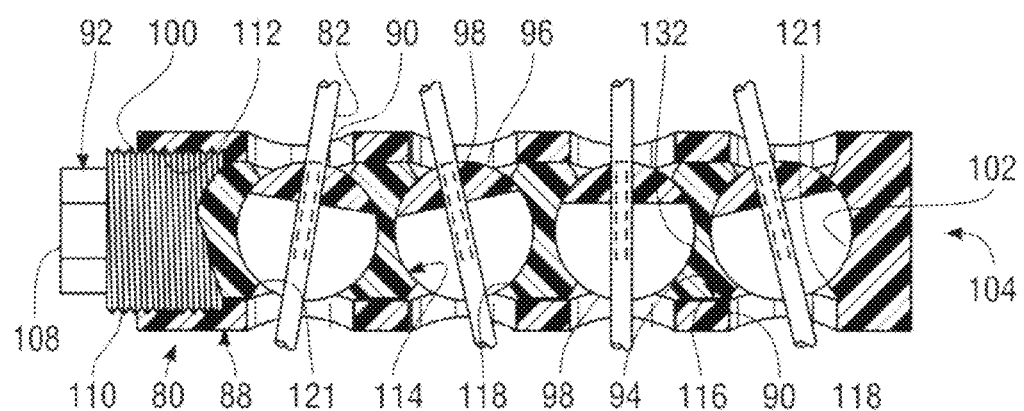
FIG. 7 is a cross-sectional side view of the device of FIG. 5.

Features of the device 80 will now be discussed with reference being made to FIGS. 6 and 7. FIG. 6 is a plan view of the device 80, while FIG. 7 is a cross-sectional side elevation thereof. The housing 88 includes a single internal mounting surface 94, with the single clamping member 92, clamping each of a plurality of pin holders 96 in place within the first internal mounting surface 94 and deflecting a deformable portion 98 of each of the pin holders 96 to hold the bone pin 82 therein in place. For example, the first internal mounting surface 94 is formed as an elongated cylinder having an open end 100 and a closed end 102, with the plurality of pin holders 96 disposed in a first row 104 within the first internal mounting surface 94. The first clamping member 92 is movable within the open end 100 of the elongated cylinder to provide a clamping force acting against the pin holder adjacent the open end 100 of the internal mounting surface 94. For example, the first clamping member is moved in the direction of arrow 106 by turning a non-circular portion 108 of the clamping member with a threaded portion 110 thereof in engagement with a threaded portion 112 of the housing 88. A clamping force, arising from the engagement between the clamping member 92 and the pin holder 96 adjacent the open end 100, is transmitted between the pin holders 96 adjacent one another within the first row 104. For example, the device 80 may be provided with a socket head wrench for loosening and tightening the clamping member 92.

Figure 8:
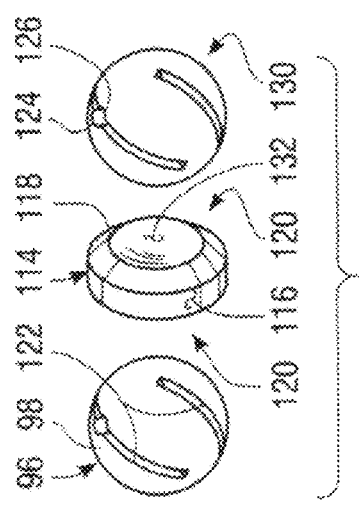
FIG. 8 is an exploded perspective views of adjacent pin holders and a spacer disposed therebetween within the device of FIG. 5

FIG. 8 is an exploded perspective view of two pin holders 96 and a spacer 114 disposed between the pin holders 96. Preferably, the device 80 additionally includes a spacer 114 between each pair of pin holders 96 adjacent one another in the first row 104, with the clamping force being transmitted between the pin holders 96 adjacent one another through the spacer 114. The spacer 114 includes a peripheral surface 116 engaging the first internal mounting surface 94 of the housing 88 between adjacent apertures 90 within the housing 88 and a circular edge 118 engaging the adjacent pin holder 96 at each side 120 of the spacer 114 to hold the pin holder 96 in place within the housing 88. Without the spacers 114, the pin holders 96 would be allowed to move into the adjacent apertures 90, so that the pin holders 96 would not be rigidly mounted within the first mounting surface 94. Preferably, as shown in FIG. 7, the first clamping member 92 and the closed end 102 of the first internal mounting surface 94 additionally also include a circular edge 121 engaging the adjacent pin holder 96 to hold the pin holder 96 in place within the housing 88.

Each of the pin holders 96 additionally includes a slot 122 extending inward from each end 124 of a pin mounting hole 126 to form a part of the deformable portion 98 of the pin holder 96 at each end 124 of the pin mounting hole 128. The slots 122 at each end 124 of the pin mounting hole 128 extend along the pin mounting hole 126, being disposed perpendicular to one another. Preferably, the slots 122 are formed to extend inward, across one another in a central portion 130 of the pin holder 96, so that the central portion 130 can be deflected by contact with a concave surface 132 of the spacer 114, even if one of the slots 122 is positioned to extend between the concave surfaces 132 of spacers 114 at either side of the pin holder 96.

Thus, each of the bone pins 82 extends through an aperture 90 within the housing 88 at angles, in directions perpendicular to one another, that can be varied by rotation of the spherically rounded pin holder 96 through which the bone pin 28 extends within the internal mounting surface 94. A bone pin may extend in a direction perpendicular to the aperture 90 or at an angle of inclination relative to such a direction of, for example, up to thirty degrees.

Figure 9:
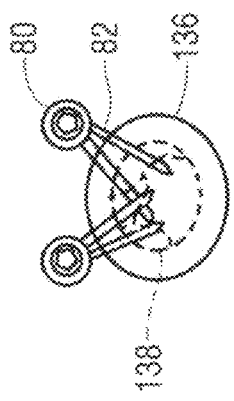
FIG. 9 is a partly sectional end view of a finger having two of the devices of FIG. 5 attached to bone fragments.

FIG. 9 is a partly sectional end view of a finger 136 with two of the devices 80 holding bone pins 82 in engagement with bone fragments 138. Two or more of the devices 80 may be used in this way so that the bone pins 82 can be directed from various locations extending around the bone fragments.

While the pin holders 96, 134 have been described in terms of use with the device 90 of FIGS. 5-7, it is understood that such pin holders 96, 134 can alternately be used with a device otherwise as described above in reference to FIGS. 1-3, with deformable portions 98, 150 being deflected in response to tightening the clamping member 30 to hold pins in place within the pin holders 56, 134.

Figure 10:
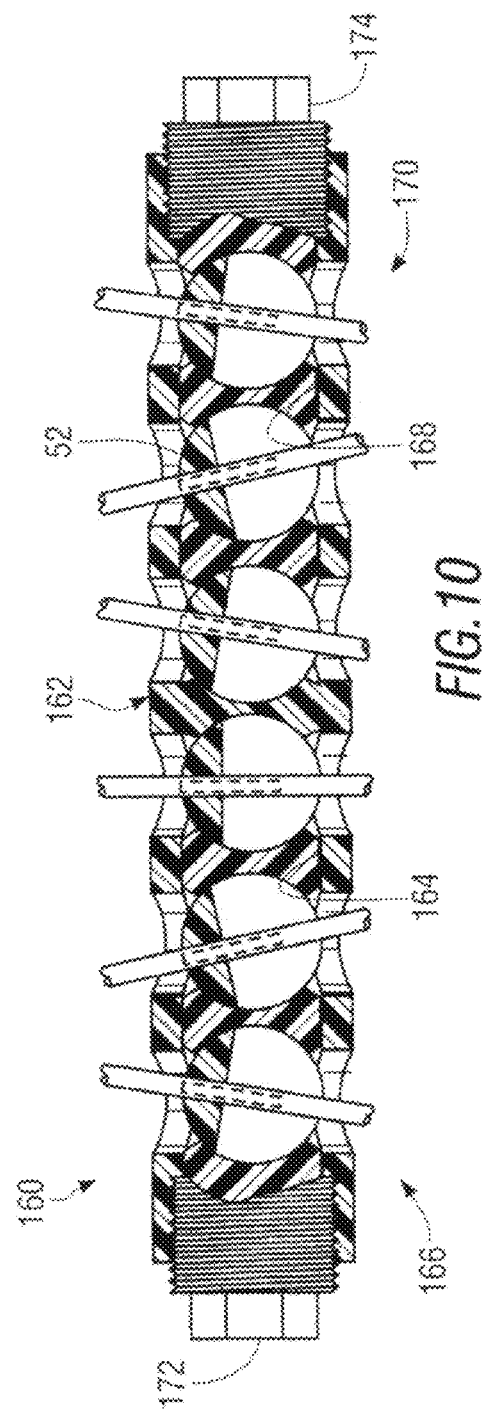
FIG. 10 is a cross-sectional side view of a device built in accordance with a second version of the second embodiment of the invention.

FIG. 10 is a cross-sectional side elevation of a device 160 built in accordance with a second version of the second embodiment of the invention to include a housing 162 having both a first internal mounting surface 164 holding a plurality of pin holders 52 in a first row 166 and a second internal mounting surface 168 holding a plurality of pin holders 52 in a second row 170. The device 160 additionally includes a first clamping device 172, which is turned to clamp and release all of the pin holders 52 in the first row 166, and a second clamping device 174, which is used to clamp and release all of the pin holders 52 in the second row 170. Other features of the device 100 are as described above in reference to FIGS. 5-9 for the device 80 built in accordance with the first version of the second embodiment of the invention. While the example of FIG. 10 shows three pin holders 52 held within each of the internal mounting surfaces 168, it is understood that each of the internal mounting surfaces in general can be configured to hold two or more pin holders 52.

Figure 11:
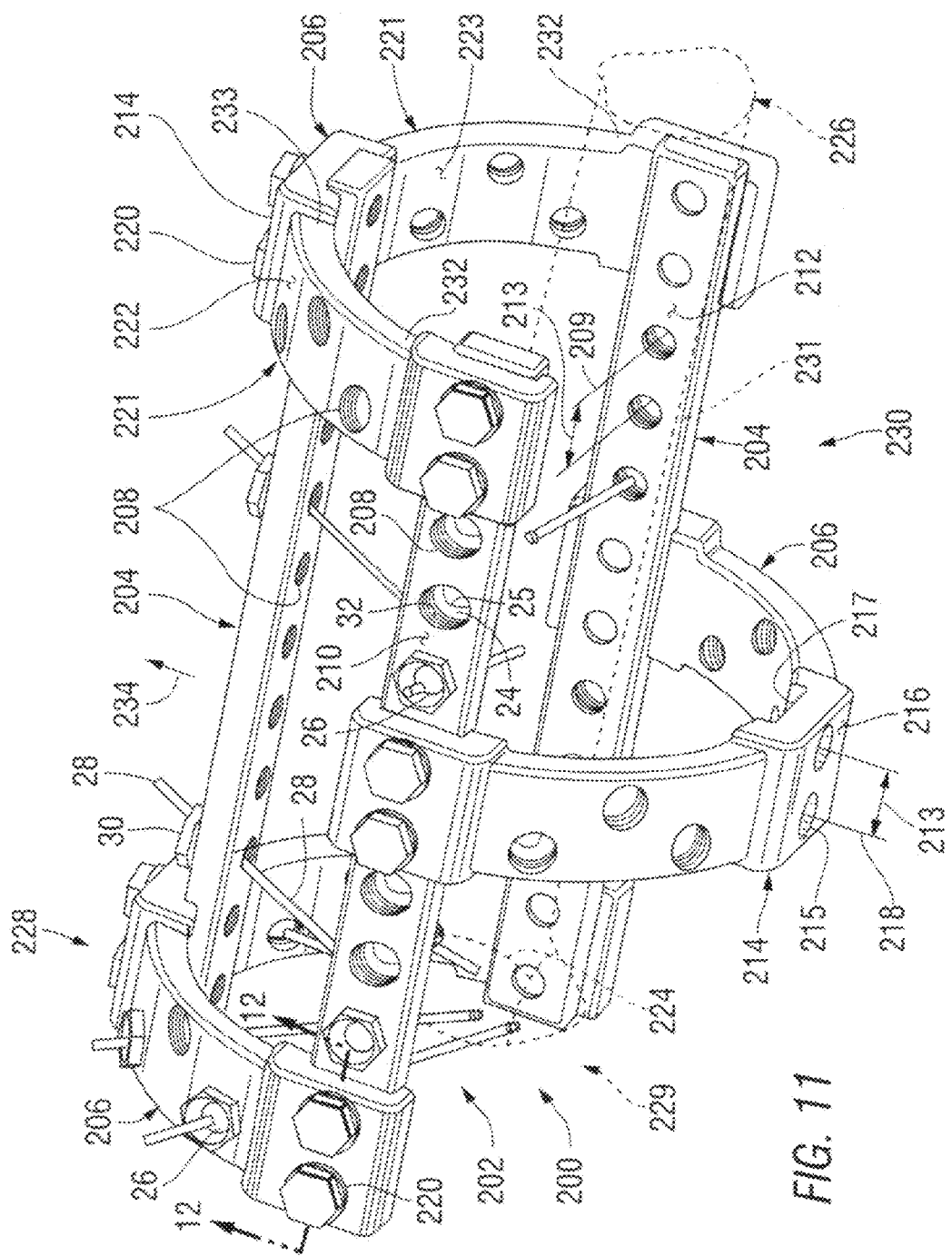
FIG. 11 is a perspective view of bone fixation apparatus built in accordance with a third embodiment of the invention from interchangeable parts.

FIG. 11 is a perspective view of bone fixation apparatus 200 built in accordance with a third embodiment of the invention from a number of interchangeable parts. This method is particularly desirable, since the parts can be assembled in many different was to meet the need for fixation in different types of fractures. In the configuration of FIG. 11, the bone fixation apparatus 200 includes a housing 202 comprising three identical inner frame members 204, and three identical outer frame members 206. Each of the inner frame members 204 and each of the outer frame members 206 includes a plurality of pin mounting structures 208, each configured as described above in reference to FIG. 2 to include an internal mounting surface 24, an aperture 25, and a threaded surface 32, with the internal mounting surface 24, the aperture 25, and the threaded surface 32 being aligned coaxially along an axis 209 of the pin mounting structure 208. In each of the inner frame members 204, the pin mounting structures 208 extend between an outer surface 210 and an inner surface 212, being aligned along the length of the inner frame member 206, and being spaced apart according to a first spacing distance 213 between the axes 210 of adjacent pin mounting structures 208. For example, the first spacing distance 213 is 2.54 cm (1 inch).

FIG. 12 is a fragmentary cross-sectional elevation of the bone fixation apparatus 200, taken as indicated by section lines 12-12 in FIG. 11 to show the means for attaching one of the inner frame members 204 to one of the outer frame members 206. Each of the outer frame members 206 includes three attachment sections 214, with each of the attachment sections 214 having a pair of attachment holes 215. extending between an outer surface 216 and an inner surface 217. The axes 218 of the attachment holes 215 are separated by the first spacing distance 213, so that attachment bolts 220 placed within the attachment holes 216 can be fastened in engagement with the threaded surfaces 32 of any adjacent pin mounting structures 208 within an inner frame member 204.

Each of the outer frame members 206 includes a pair of arcuate sections 221, in which a number of pin mounting structures 208 extend from an outer surface 222 to an inner surface 223. Each of the pin mounting structures 208 that is not used for the attachment of an inner frame member 204 to one of the outer frame members 206 may be used fo hold a bone pin 28 that has been surgically attached to a bone fragment in place, using a pin holder 26 and a clamping member 30, again as described above in reference to FIG. 2. The fixation apparatus 200 is particularly well suited for the external fixation of a number of fragments 224 of a long bone 226. As shown in the example of FIG. 11, a first plurality 228 of bone pins 28 attached to fragments 224 at an end 229 of the bone 226 are held in place within one of the outer frame members 206, while a second plurality 230 of bone pins 28 attached to a shank 231 of the bone 226 are held in place within the inner frame members 204.

Other frame members 204, 206 not used to fasten individual bone pins 28 in place may be included within the bone fixation apparatus 200 to provide structural strength and stability. In the example of FIG. 11, three outer frame members are attached to three inner frame members 204, with two the inner frame members 204 being attached at the attachment sections 214 disposed at outer ends 232 of the arcuate sections 221 in each of the outer members 206. The remaining inner frame member 204 is attached to the attachment section 214 disposed between inner ends 233 of the arcuate sections 221. Two of the outer frame members extend in a common direction, indicated by arrow 236, while the other outer frame member 206 extends opposite the direction of arrow 236.

FIG. 13 is a perspective view of bone fixation apparatus 250 built in accordance with a fourth embodiment of the invention from a number of interchangeable parts, including parts described above in reference to FIGS. 2-4, 11, and 12, with like parts and similar features being accorded like reference numbers. The bone fixation apparatus 250, which is particularly suited for the fixation of fractured bones within a foot, includes a housing 252 comprising an outer frame member 254, a pair of inner frame members 204, and three cross members 256. The outer frame member 254 includes an arcuate section 258, an attachment section 214 at each end 260 of the arcuate section, and a straight section 262, extending forward, in the direction of arrow 264, from each of the attachment sections 214. The arcuate section 258 includes a plurality of pin mounting structures 208, each extending between an outer surface 266 and an inner surface 268. Each of the straight sections 262 includes an upper row 270 and a lower row 272 of pin mounting structures 208, each extending between an outer surface 274 and an inner surface 276. Each of the cross members 256 includes an arcuate section 278 having a plurality of pin mounting structures 208, each extending between an outer surface 280 and an inner surface 282, and a mounting block 284 at each end 286 of the arcuate section 278. Each inner frame member 204, which is configured as described above in reference to FIG. 11, is fastened within one of the attachment sections 214 of the outer frame member 254, in the manner generally described above in reference to FIG. 12.

FIG. 14 is a fragmentary cross-sectional elevation of the bone fixation apparatus 250, taken as indicated by section lines 14-14 in FIG. 13 to show the means for attaching an attachment block 284 of a cross member 256 to one of the straight sections 262 of the outer frame member 254. A single attachment screw 220 is used for this purpose, being driven into engagement with the threaded surface 32 of a pin mounting structure 208 within the upper row 270 such structures 208 within the straight section 262. A ledge 288 of the attachment block 284 rests against an upper surface 290 of the straight section 262 to prevent rotation of the cross member 256 about the axis 292 of the attachment screw 220.

Each of the pin mounting structures 208 that is not used with an attachment screw 220 can be used with a clamping member 30 and a pin holder 26, as described above in reference to FIG. 2, to hold a pin 28 that has been surgically attached to a bone or bone fragment. For example, pins 28 attached to phalanges 292 and metatarsal bones 294 may be held within the straight sections 262 of the outer frame 254 and within the cross members 256, while the bone fixation apparatus 250 is supported by pins 28 attached to the tibia 296 and held within the inner frame members 204. Pins 28 attached in the ankle and heel areas 298 may be held in pin mounting structures 208 within the inner frame members 204 and the arcuate section 256 of the outer frame member 254. The actual locations and configuration of the pins 28 is determined according to the location of bone fractures, with the housing 252 being additionally configurable by arranging the number and locations of cross members 256.

Figure 15:
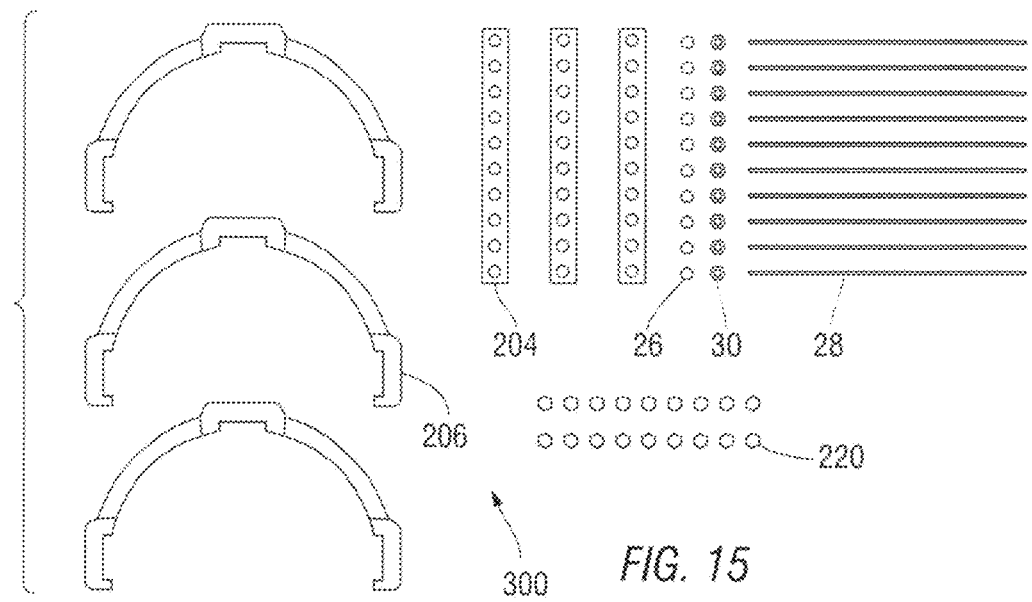
FIG. 15 is a view of a kit including elements to form the bone fixation apparatus of FIG. 11.
Figure 16:
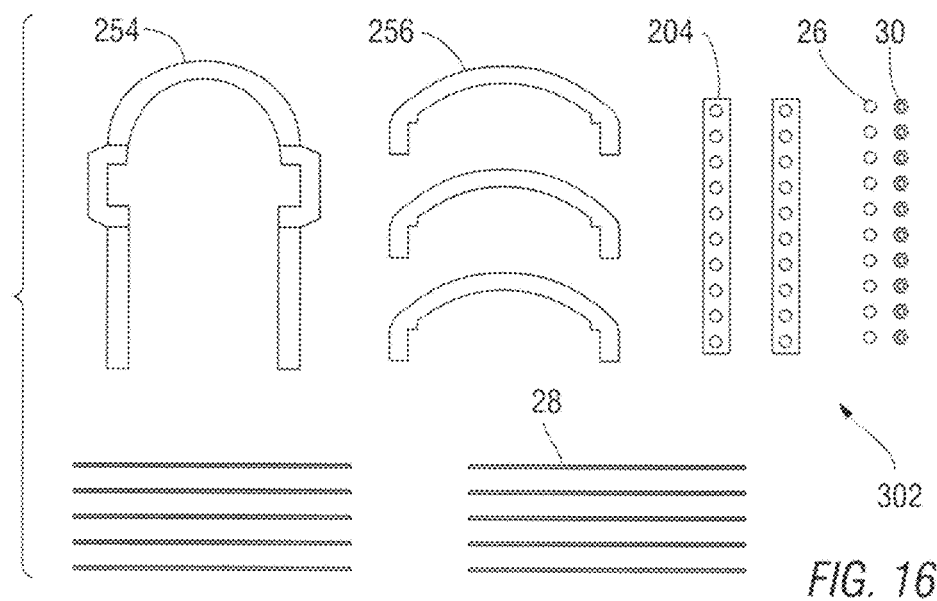
FIG. 16 is a view of a kit including elements to form the bone fixation apparatus of FIG. 13.

FIG. 15 is a view of a kit 300 including elements to form the bone fixation apparatus 200, as described above in reference to FIG. 11; and FIG. 16 is a view of a kit 302 including elements to form the bone fixation apparatus 250, as described above in reference to FIG. 13.

While the invention has been described in terms of preferred embodiments and versions thereof with some degree of specific, it is understood that this description has been given only by way of example, and that many changes can be made without departing from the spirit and scope of the invention, as described in the appended claims.

What is claimed is:

1. Apparatus for external fixation of bone fragments, wherein the apparatus comprises:
at least two inner frame members including a straight section having an inner surface, an outer surface, and a plurality of pin mounting structures, wherein each pin mounting structure includes an internal mounting surface, an aperture extending from the internal mounting surface to the inner surface, and a threaded surface extending from the internal mounting surface to the outer surface, wherein the internal mounting surface, the aperture, and the threaded surface are aligned coaxially along an axis of the pin mounting structure, and wherein the axes of adjacent pin mounting structures within the plurality are each separated along a length of the straight section by a first separation distance;
an outer frame member comprising an arcuate section, an attachment section at each end of the arcuate section, and a straight section extending in a forward direction from an end of each of the attachment sections, wherein each of the attachment sections has an inner surface, an outer surface, and two attachment holes, wherein each attachment hole extends along an axis from the inner surface to the outer surface, wherein the axes of the attachment holes are separated along a width of the attachment section by the first separation distance, wherein each of the straight sections has an inner surface, an outer surface, and a plurality of pin mounting structures, and wherein the outer frame member is attached to each of the at least two inner frame members with the two attachment holes of each attachment section aligned with two adjacent pin mounting structures within a respective inner frame member;
at least four attachment bolts, each extending through one of the attachment holes to engage the threaded surface within one of the adjacent pin mounting structures, wherein the inner frame members are each attached to one of the attachment sections of one of the outer frame members using two of the attachment bolts; and
at least one pin assembly including a pin holder, a bone pin, and a clamping member, wherein the clamping member engages the threaded surface of a pin mounting structure in the plurality of pin mounting structures to hold the pin holder in place within the internal mounting surface, and wherein the pin holder holds the bone pin.

2. The apparatus of claim 1, additionally comprising:
at least one cross member extending between the straight sections of the outer frame member, wherein each cross member includes an arcuate section having an outer surface, an inner surface, and a plurality of the pin mounting structures, and wherein each cross member additionally includes an attachment block at each end of the arcuate section with a ledge contacting one of the straight sections to prevent rotation of the cross member relative to the straight section; and
two attachment bolts, each extending through one of the attachment holes in each cross member to engage the threaded surface within one of the adjacent pin mounting structures in one of the straight sections of the outer frame member.

3. Apparatus for external fixation of bone fragments, wherein the apparatus comprises:
at least two inner frame members, each including a straight section having an inner surface, an outer surface, and a plurality of pin mounting structures, wherein each pin mounting structure includes an internal mounting surface, an aperture extending from the internal mounting surface to the inner surface, and a threaded surface extending from the internal mounting surface to the outer surface, wherein the internal mounting surface, the aperture, and the threaded surface are aligned coaxially along an axis of the pin mounting structure, and wherein the axes of adjacent pin mounting structures within the first plurality are each separated along a length of the straight section by a first separation distance;

at least two outer frame members, each including two arcuate sections and three attachment sections, wherein each of the arcuate sections includes an outer surface, an inner surface, and a plurality of pin mounting structures, wherein each of the attachment sections has an inner surface, an outer surface, and two attachment holes, wherein each attachment hole extends along an axis from the inner surface to the outer surface, wherein the axes of the attachment holes are separated along a width of the attachment section by the first separation distance, wherein each of the two arcuate sections has an inner end and an outer end, wherein one of the attachment sections is disposed between the inner ends of the two arcuate sections; and wherein one of the attachment sections is disposed at each outer end of the two arcuate sections;

a plurality of attachment bolts, each extending through one of the attachment holes to engage the threaded surface within one of the adjacent pin mounting structures, wherein each outer frame member is attached to each of the at least two inner frame members with the two attachment holes of a respective attachment section aligned with two adjacent pin mounting structures within a respective inner frame member; wherein the outer frame members are fastened to extend between the inner frame members, wherein the outer frame members are connected by the inner frame members extending between the attachment sections disposed at the outer ends of the arcuate structures, and wherein the outer frame members extend in opposite directions from the inner frame members; and at least one pin assembly including a pin holder, a bone pin, and a clamping member, wherein the clamping member engages the threaded surface of a pin mounting structure in the plurality of pin mounting structures to hold the pin holder in place within the internal mounting surface of the pin mounting structure, and wherein the pin holder holds the bone pin.

4. The apparatus of claim 3, wherein each pin holder includes:
   a pin mounting hole through which a bone pin extends;
   a spherically rounded external surface engaging the internal mounting surface within one of the pin mounting structures; and
   a first slot extending perpendicular to the pin mounting hole across the pin mounting hole and partially across the pin holder, displaced inward from a first end of the pin mounting hole, forming a first deflectable portion of the pin holder extending between the first slot and the first end of the pin mounting hole.

5. The apparatus of claim 4, wherein each pin holder additionally includes a second slot extending perpendicular to the pin mounting hole across the pin mounting hole and partially across the pin holder, displaced inward from a second end of the pin mounting hole, opposite the first end, forming a second deflectable portion of the pin holder extending between the second slot and the second end of the pin mounting hole.

6. A kit for building an apparatus for external fixation of bone fragments, wherein the kit comprises:
   a plurality of inner frame members, each including a straight section having an inner surface, an outer surface, and a plurality of pin mounting structures, wherein each of the pin mounting structures includes an internal mounting surface, an aperture extending from the internal mounting surface to the inner surface, and a threaded surface extending from the internal mounting surface to the outer surface, wherein the internal mounting surface, the aperture, and the threaded surface are aligned coaxially along an axis of the internal mounting surface, and wherein the axes of adjacent pin mounting structures within the plurality are each separated along a length of the straight section by a first separation distance;

an outer frame member including an arcuate section and at least two attachment sections, wherein each attachment section has an inner surface, an outer surface, and two attachment holes, wherein each attachment hole extends along an axis from the inner surface to the outer surface, wherein the axes of the attachment holes are separated along a width of the attachment section by the first separation distance, wherein the outer frame member is configured to be attached to each inner frame member with the two attachment holes of a respective attachment section aligned with two adjacent pin mounting structures within a respective inner frame member, wherein one of the attachment sections is disposed at each end of the arcuate section, wherein the outer frame member additionally comprises a straight section extending in a forward direction from an end of each of the attachment sections, wherein each of the straight sections has an inner surface, an outer surface, and a plurality of pin mounting structures, wherein each of the pin mounting structures in the outer frame member includes a internal mounting surface, an aperture extending from the internal mounting surface to the inner surface, and a threaded surface extending from the internal mounting surface to the outer surface, and wherein the internal mounting surface, the aperture, and the threaded surface are aligned coaxially along an axis of each of the pin mounting structures within the outer frame member;

at least one cross member configured to extend between the straight sections of the outer frame member, wherein each of the at least one cross member includes an arcuate section, including an outer surface, an inner surface, and a plurality of pin mounting structures, wherein each cross member additionally includes an attachment block at each end of the arcuate section and wherein each of the pin mounting structures in each cross member includes an internal mounting surface, an aperture extending from the internal mounting surface to the inner surface, and a threaded surface extending from the internal mounting surface to the outer surface, wherein the internal mounting surface, the aperture, and the threaded surface of each of the pin mounting structures in the cross member are aligned coaxially along an axis of the internal mounting surface, and wherein each attachment block includes a mounting hole and a rail engaging shelf configured to prevent rotation of the cross member by contact with a surface of one of the straight sections;

a plurality of attachment bolts, each configured to extend through one of the attachment holes to engage the threaded surface within one of the pin mounting structures of the inner frame members;

a plurality of bone pins;

a plurality of pin holders, each configured to engage a bone pin in the plurality of bone pins extending through the pin mounting structures, and to engage the internal mounting surface of a pin mounting structure in the plurality of pin mounting structures; and a plurality of clamping members, each configured to engage the threaded surface of an internal mounting surface in the plurality of pin mounting structures.

7. The kit of claim 6, wherein each pin holder includes:
a pin mounting hole configured to hold one of the bone pins;
a spherically rounded external surface configured to engage the internal mounting surface within one of the pin mounting structures; and
a first slot extending perpendicular to the pin mounting hole across the pin mounting hole and partially across the pin holder, displaced inward from a first end of the pin mounting hole, forming a first deflectable portion of the pin holder extending between the first slot and the first end of the pin mounting hole.

8. The apparatus of claim 7, wherein each pin holder additionally includes a second slot extending perpendicular to the pin mounting hole across the pin mounting hole and partially across the pin holder, displaced inward from a second end of the pin mounting hole, opposite the first end, forming a second deflectable portion of the pin holder extending between the second slot and the second end of the pin mounting hole.

9. A method for external fixation of bone fragments, wherein the method comprises:
attaching a plurality of inner frame members to a plurality of attachment sections of an outer frame member with a pair of attachment bolts extending through a pair of attachment holes extending along axes separated by a first separation distance within each attachment section to engage each of the inner frame members, wherein each of the inner frame members includes a straight section having an inner surface, an outer surface, and a plurality of pin mounting structures, wherein each of the pin mounting structures includes an internal mounting surface, an aperture extending from the internal mounting surface to the inner surface, and a threaded surface extending from the internal mounting surface to the outer surface, wherein the internal mounting surface, the aperture, and the threaded surface are aligned coaxially along an axis of the internal mounting surface, wherein the axes of adjacent pin mounting structures within the plurality are each separated along a length of the straight section by the first separation distance, wherein the attachment bolts engage a pair of the threaded surfaces within each of the inner frame members, wherein the outer frame member additionally comprises a straight section extending in a forward direction from an end of each of the attachment sections, wherein each of the straight sections has an inner surface, an outer surface, and a plurality of pin mounting structures, wherein each of the pin mounting structures in the outer frame member includes an internal mounting surface, an aperture extending from the internal mounting surface to the inner surface, and a threaded surface extending from the internal mounting surface to the outer surface, and wherein the internal mounting surface, the aperture, and the threaded surface are aligned coaxially along an axis of each of the pin mounting structures within the outer frame member;
attaching a plurality of cross members to extend between the straight sections of the outer frame member, wherein each cross member includes an arcuate section, including an outer surface, an inner surface, and a plurality of pin mounting structures, wherein each cross member additionally includes an attachment block at each end of the arcuate section, wherein each of the pin mounting structures in each cross member includes an internal mounting surface, an aperture extending from the internal mounting surface to the inner surface, and a threaded surface extending from the internal mounting surface to the outer surface, wherein the internal mounting surface, the aperture, and the threaded surface of each of the pin mounting structures in the cross member are aligned coaxially along an axis of the internal mounting surface, and wherein each attachment block includes a mounting hole and a rail engaging surface;
surgically implanting a plurality of bone pins within the bone fragments to extend outward through a plurality of the pin mounting structures within the inner frame members;
placing a pin holder over each of the bone pins to engage the internal mounting surface in the pin mounting structure through which the bone pin extends; and
tightening a clamping member engaging the threaded surface of each pin mounting structure through which the bone pin extends to hold the pin holder in place within the internal mounting surface and to hold the bone pin in place within the pin holder.

10. The method of claim 9, wherein each pin holder includes:
a pin mounting hole configured to hold one of the bone pins;
a spherically rounded external surface configured to engage the internal mounting surface within one of the pin mounting structures; and
a first slot extending perpendicular to the pin mounting hole across the pin mounting hole and partially across the pin holder, displaced inward from a first end of the pin mounting hole, forming a first deflectable portion of the pin holder extending between the first slot and the first end of the pin mounting hole.

11. The apparatus of claim 10, wherein each pin holder additionally includes a second slot extending perpendicular to the pin mounting hole across the pin mounting hole and partially across the pin holder, displaced inward from a second end of the pin mounting hole, opposite the first end, forming a second deflectable portion of the pin holder extending between the second slot and the second end of the pin mounting hole.

* * * * *